US010646302B2

(12) United States Patent
Tamura et al.

(10) Patent No.: US 10,646,302 B2
(45) Date of Patent: May 12, 2020

(54) MEDICAL OBSERVATION DEVICE

(71) Applicant: Sony Olympus Medical Solutions Inc., Tokyo (JP)

(72) Inventors: Shigeru Tamura, Tokyo (JP); Hiroki Saijo, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 480 days.

(21) Appl. No.: 15/434,434

(22) Filed: Feb. 16, 2017

(65) Prior Publication Data
US 2017/0258549 A1 Sep. 14, 2017

(30) Foreign Application Priority Data

Mar. 11, 2016 (JP) .................................. 2016-048906

(51) Int. Cl.
*A61B 90/00* (2016.01)
*A61B 90/25* (2016.01)
*B25J 9/16* (2006.01)
*A61B 90/20* (2016.01)

(52) U.S. Cl.
CPC .............. *A61B 90/37* (2016.02); *A61B 90/20* (2016.02); *A61B 90/25* (2016.02); *A61B 90/361* (2016.02); *B25J 9/162* (2013.01); *B25J 9/1689* (2013.01); *G05B 2219/41032* (2013.01); *G05B 2219/41265* (2013.01); *Y10S 901/28* (2013.01); *Y10S 901/44* (2013.01); *Y10S 901/47* (2013.01)

(58) Field of Classification Search
CPC .. A61B 2017/00398; A61B 2017/0046; A61B 17/07207; B60W 10/06
See application file for complete search history.

(56) References Cited

U.S. PATENT DOCUMENTS

| | | | | |
|---|---|---|---|---|
| 9,749,486 | B2 * | 8/2017 | Yoshimizu | ............... B65H 7/02 |
| 2007/0229005 | A1 * | 10/2007 | Ishizaki | ............. G03G 15/5008 |
| | | | | 318/400.03 |
| 2010/0239290 | A1 * | 9/2010 | Ryu | ......................... H02P 8/10 |
| | | | | 399/53 |

FOREIGN PATENT DOCUMENTS

| | | | |
|---|---|---|---|
| JP | H04-124494 | A | 4/1992 |
| JP | 06-297377 | A | 10/1994 |
| JP | 09-089052 | A | 3/1997 |

(Continued)

OTHER PUBLICATIONS

Notifications of Reasons for Refusal dated Oct. 8, 2019, issued in corresponding Japanese Application No. 2016-048906, 10 pages (with English Translation).

*Primary Examiner* — Elvin G Enad
*Assistant Examiner* — Zoheb S Imtiaz
(74) *Attorney, Agent, or Firm* — Xsensus LLP

(57) ABSTRACT

A medical observation device includes: an imaging device; a support unit that supports the image-capturing unit and includes arms and joints rotatably connecting the arms; a motor that applies power to at least one of the joints, and rotates two of the arms connected at the joint relative to each other; a gear mechanism that includes two intermeshing gears and is disposed in a power transmission path from the motor to the at least one joint; an operation receiver that receives a user operation; and a controller that performs first control for causing the motor to rotate in accordance with the user operation received by the operation receiver and performs second control after the first control is completed and rotation of the motor is stopped.

8 Claims, 9 Drawing Sheets

(56) References Cited

FOREIGN PATENT DOCUMENTS

| JP | 09-207602 A | 8/1997 |
|---|---|---|
| JP | 11-244301 | 9/1999 |
| JP | 2003-280742 A | 10/2003 |
| WO | 2015129473 A1 | 9/2015 |

* cited by examiner

MEDICAL OBSERVATION DEVICE

CROSS-REFERENCE TO RELATED APPLICATION(S)

The present application claims priority to and incorporates by reference the entire contents of Japanese Patent Application No. 2016-048906 filed in Japan on Mar. 11, 2016.

BACKGROUND

The present disclosure relates to a medical observation device.

Medical observation devices are widely used in the medical field. These medical observation devices include magnification optics for magnifying and observing a minute segment of a surgical site of a patient, and a support unit having a plurality of arms and a plurality of joints that rotatably connect the arms and supporting the magnification optics at its distal end (see Japanese Patent Application Laid-open No. 11-244301, for example).

Japanese Patent Application Laid-open No. 11-244301 discloses a medical observation device including a motor that applies power to a joint to rotate two arms connected at the joint relative to each other, and a gear mechanism including two intermeshing gears and disposed in a power transmission path from the motor to the joint. In the medical observation device disclosed in Japanese Patent Application Laid-open No. 11-244301, the motor is driven in accordance with an operation by an operator on a foot switch, and the power from the motor is applied to the joint via the gear mechanism. This power rotates the two arms connected at the joint relative to each other and the position and orientation of the magnification optics are changed accordingly, that is, the field of view is moved.

SUMMARY

To allow for dimensional tolerances or linear expansion due to thermal change, the two intermeshing gears include a backlash.

Such backlash causes the following problem.

The operator first operates the foot switch to rotate the motor in a first direction (hereinafter referred to as forward rotation), and the position and orientation of the magnification optics are changed. The two gears rotate in accordance with this operation. In this case, a first distance between first tooth surfaces that are out of meshing engagement with each other in the forward rotation coincides with an amount of backlash between the two gears, whereas a second distance between second tooth surfaces that mesh with each other in the forward rotation coincides with zero.

The operator then operates the foot switch to rotate the motor in the reverse direction that is opposite to the first direction (hereinafter referred to as reverse rotation). At this time, the first distance between the first tooth surfaces that in turn are going to mesh with each other in the reverse rotation has the same value as that of the amount of backlash between the two gears. Thus, the two gears do not mesh with each other (undergo an idle running time) until the first distance becomes zero (until the first distance is reduced to zero). In other words, the position and orientation of the magnification optics are not changed instantly. The position and orientation of the magnification optics are changed after the first distance becomes zero and the two gears mesh with each other.

As described above, when the motor is rotated in the reverse direction that is opposite to the direction in which the motor was rotated immediately before, the two gears experience an idle running time in accordance with the amount of the backlash. This idle running time prevents immediate change in the field of view.

There is a need for a medical observation device capable of changing a field of view immediately.

According to one aspect of the present disclosure, a medical observation device includes: an imaging device configured to magnify an observation target and image the magnified observation target; a support unit that supports the image-capturing unit at a distal end and includes a plurality of arms and a plurality of joints rotatably connecting the arms; a motor that is provided in the support unit, applies power to at least one of the joints, and rotates two of the arms connected at the joint relative to each other; a gear mechanism that includes two intermeshing gears and is disposed in a power transmission path from the motor to the at least one joint; an operation receiver that receives a user operation; and a controller that performs first control for causing the motor to rotate in accordance with the user operation received by the operation receiver and performs second control after the first control is completed and rotation of the motor is stopped, wherein the controller performs the second control to rotate the motor in a reverse direction that is opposite to a direction in which the motor is rotated in the first control, and to adjust a first distance between first tooth surfaces of the two gears, the first tooth surfaces meshing with each other in accordance with rotation of the motor in the reverse direction, and adjust a second distance between second tooth surfaces of the two gears, the second tooth surfaces being out of meshing engagement with each other in accordance with the rotation of the motor in the reverse direction, to a smaller value than an amount of backlash between the two gears.

DETAILED DESCRIPTION OF THE PREFERRED EMBODIMENT

An embodiment of the present disclosure (hereinafter the embodiment) is described below with reference to the accompanying drawings. The embodiment described below is not intended to limit the scope of the present disclosure. Like reference signs are assigned to like parts in the accompanying drawings.

Schematic Configuration of Medical Observation System

Figure 1:
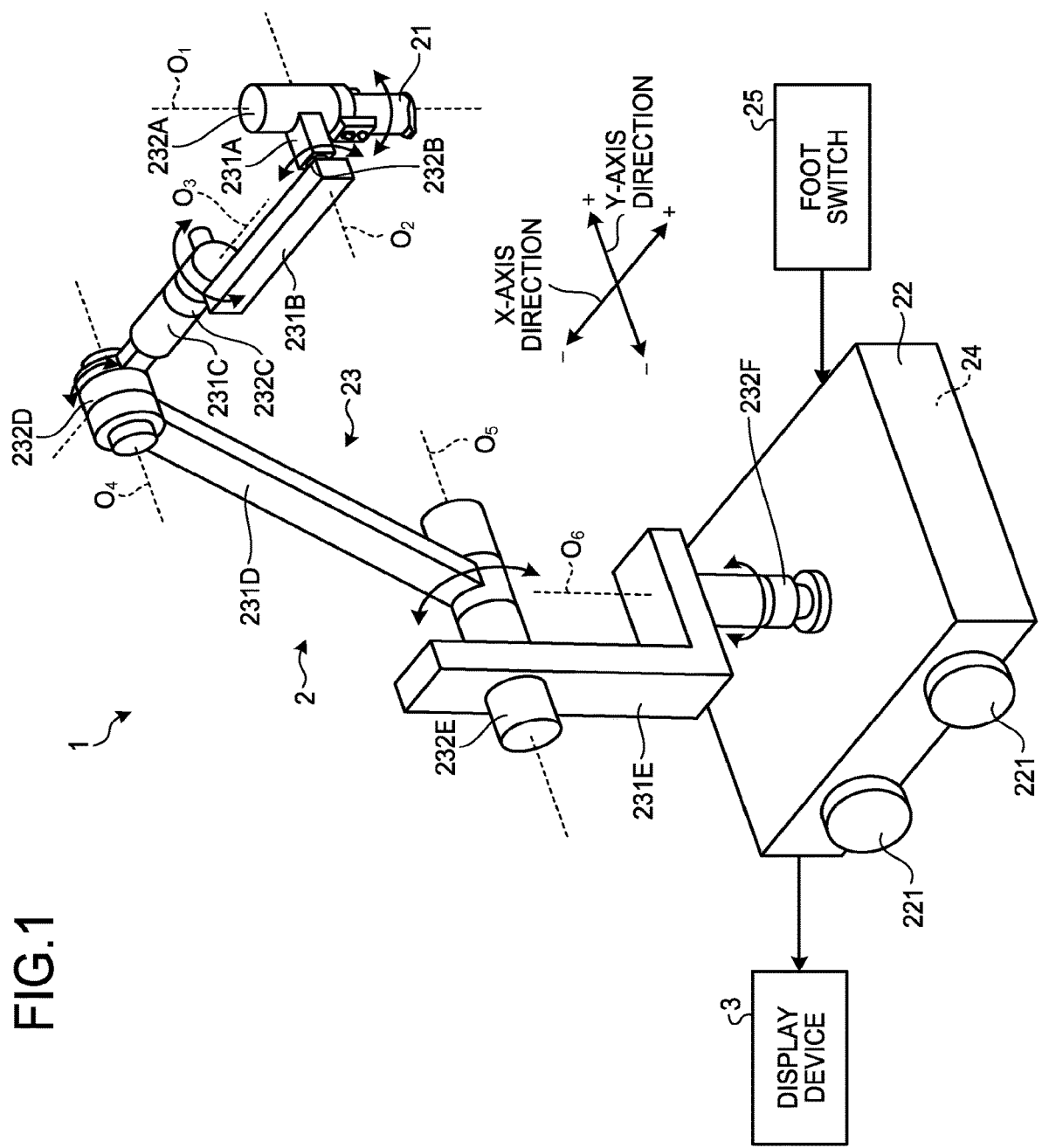
FIG. 1 is a diagram illustrating a schematic configuration of a medical observation system according to an embodiment of the present disclosure.

FIG. 1 is a diagram illustrating a schematic configuration of a medical observation system 1 according to an embodiment of the present disclosure.

The medical observation system 1 is a system for magnifying and capturing an image of a site (observation target) on which an operator performs operation or examination, and displaying an image in accordance with the image-capturing operation. As illustrated in FIG. 1, the medical observation system 1 includes a medical observation device 2 that captures an image of an observation target and outputs an image signal, and a display device 3 that displays an image on the basis of the image signal output from the medical observation device 2.

As illustrated in FIG. 1, the medical observation device 2 includes a microscope 21, a base unit 22, a support unit 23, a controller 24, and a foot switch 25.

The microscope 21 magnifies the observation target and captures an image of it, and outputs an image signal corresponding to the captured image. The microscope 21 includes, for example, any known optical system and any known imaging device, such as charge coupled device (CCD) or complementary metal oxide semiconductor (CMOS), that receives light collected by the optical system and converts the light into an electric signal. The microscope 21 has various functions such as an auto-focus (AF) function and an optical zooming function. The microscope 21 may be configured as what is called a stereo camera including a pair of imaging devices.

The base unit 22 is a base on which the medical observation device 2 stands, and is movable on the floor with casters 221 (FIG. 1).

The support unit 23 extends from the base unit 22 and holds the microscope 21 at its distal end (an end away from the base unit 22). The support unit 23 may three-dimensionally move the microscope 21 in accordance with the operation by the operator.

In the present embodiment, the support unit 23 is configured to move the microscope 21 along six degrees of freedom, but is not limited to this. The support unit 23 may be configured to move along any different number of degrees of freedom.

As illustrated in FIG. 1, the support unit 23 includes first to fifth arms 231A to 231E and first to sixth joints 232A to 232F.

The first to sixth joints 232A to 232F, which are not specifically illustrated in FIG. 1, each include a fixed part, a moving part, and a bearing interposed between the fixed part and the moving part. The moving part is rotatable relative to the fixed part via the bearing.

The first joint 232A is disposed at the distal end of the support unit 23 and has a cylindrical shape. The first joint 232A holds the microscope 21 at its moving part (not illustrated) disposed inside the cylinder. The first joint 232A is supported by the first arm 231A through the fixed part (not illustrated) disposed outside of the cylinder. The moving part of the first joint 232A is rotatable about a first axis $O_1$ relative to the fixed part via the bearing (not illustrated). Thus, the first joint 232A allows the microscope 21 to rotate about the first axis $O_1$.

The first axis $O_1$ is the central axis of the cylindrical first joint 232A, and coincides with the optical axis of the microscope 21 held by the first joint 232A.

In other words, rotating the microscope 21 about the first axis $O_1$ changes the orientation of the imaging field of view of the microscope 21.

The first arm 231A extends from a side surface of the first joint 232A in a direction orthogonal to the first axis $O_1$, and supports the first joint 232A (fixed part) at an end.

The second joint 232B connects the first arm 231A with the second arm 231B such that the moving part (not illustrated) of the second joint 232B disposed close to the distal end is attached to the base end of the first arm 231A and the fixed part (not illustrated) disposed close to the base end (close to the base unit 22) is attached to the second arm 231B. The moving part of the second joint 232B is rotatable about a second axis $O_2$ relative to the fixed part via the bearing (not illustrated). Thus, the second joint 232B allows the first arm 231A (microscope 21) to rotate about the second axis $O_2$.

The second axis $O_2$ is orthogonal to the first axis $O_1$, and parallel to the direction in which the first arm 231A extends.

In other words, rotating the microscope 21 about the second axis $O_2$ changes the direction of the optical axis of the microscope 21 relative to the observation target. That is, the imaging field of view of the microscope 21 is moved in the X-axis direction (FIG. 1). The second joint 232B is a joint for moving the imaging field of view of the microscope 21 in the X-axis direction (+X direction or −X direction).

The second arm 231B extends in a direction orthogonal to the first axis $O_1$ and the second axis $O_2$, and supports the second joint 232B (fixed part) at its distal end.

The third joint 232C connects the second arm 231B with the third arm 231C such that the moving part (not illustrated) of the third joint 232C disposed close to the distal end is attached to the base end of the second arm 231B and the fixed part (not illustrated) disposed close to the base end is attached to the third arm 231C. The moving part of the third joint 232C is rotatable about a third axis $O_3$ relative to the fixed part via the bearing (not illustrated). Thus, the third joint 232C allows the second arm 231B (microscope 21) to rotate about the third axis $O_3$.

The third axis $O_3$ is orthogonal to the first axis $O_1$ and the second axis $O_2$ (parallel to the direction in which the second arm 231B extends).

In other words, rotating the microscope 21 about the third axis $O_3$ changes the direction of the optical axis of the microscope 21 relative to the observation target. That is, the imaging field of view of the microscope 21 is moved in the Y-axis direction (FIG. 1) orthogonal to the X-axis direction. The third joint 232C is a joint for moving the imaging field of view of the microscope 21 in the Y-axis direction (+Y direction or −Y direction).

The third arm 231C extends in a direction substantially parallel to the direction in which the second arm 231B extends, and supports the third joint 232C (fixed part) at its distal end.

The fourth joint 232D extends in a direction substantially parallel to the second axis $O_2$, and connects the third arm 231C with the fourth arm 231D such that the moving part (not illustrated) of the fourth joint 232D disposed at an end is attached to the base end of the third arm 231C and the fixed part (not illustrated) disposed at the opposite end is attached to the fourth arm 231D. The moving part of the fourth joint 232D is rotatable about a fourth axis $O_4$ relative to the fixed part via the bearing (not illustrated). Thus, the fourth joint 232D allows the third arm 231C (microscope 21) to rotate about the fourth axis $O_4$.

The fourth axis $O_4$ is orthogonal to the third axis $O_3$, and parallel to the second axis $O_2$.

In other words, rotating the microscope 21 about the fourth axis $O_4$ changes the height of the microscope 21 relative to the observation target.

The fourth arm 231D is orthogonal to the fourth axis $O_4$, linearly extends toward the base unit 22, and supports the fourth joint 232D (fixed part) at its distal end.

The fifth joint 232E extends in a direction substantially parallel to the fourth axis $O_4$, and connects the fourth arm 231D with the fifth arm 231E such that the moving part (not illustrated) of the fifth joint 232E disposed at an end is attached to the base end of the fourth arm 231D and the fixed part (not illustrated) disposed at the opposite end is attached to the fifth arm 231E. The moving part of the fifth joint 232E is rotatable about a fifth axis $O_5$ relative to the fixed part via the bearing (not illustrated). Thus, the fifth joint 232E allows the fourth arm 231D (microscope 21) to rotate about the fifth axis $O_5$.

The fifth axis $O_5$ is parallel to the fourth axis $O_4$.

The fifth arm 231E is a substantially L-shaped arm including a first portion extending in the vertical direction and a second portion extending from the first portion at a right angle, and supports the fifth joint 232E (fixed part) at the first portion.

The sixth joint 232F extends in the vertical direction, and connects the fifth arm 231E with the base unit 22 such that the moving part (not illustrated) of the sixth joint 232F disposed at an end is attached to the second portion of the fifth arm 231E and the fixed part (not illustrated) disposed at the opposite end is fixed to the upper surface of the base unit 22. The moving part of the sixth joint 232F is rotatable about a sixth axis $O_6$ relative to the fixed part via the bearing (not illustrated). Thus, the sixth joint 232F allows the fifth arm 231E (microscope 21) to rotate about the sixth axis $O_6$.

The sixth axis $O_6$ extends along the vertical direction.

The controller 24 is disposed inside the base unit 22. The controller 24 is configured by, for example, a central processing unit (CPU). The controller 24 collectively controls the operations of the medical observation system 1.

Specifically, the controller 24 switches modes of operation of the support unit 23 in accordance with a user operation performed by the operator on an operation-changing switch (not illustrated) provided on the microscope 21, and performs processing in accordance with the switched mode of operation.

In the present embodiment, the modes of operation of the support unit 23 include a fixing mode, a free movement mode, and an XY movement mode.

The fixing mode is a mode of operation in which rotation of the moving parts of the first to sixth joints 232A to 232F relative to the respective fixed parts is stopped by brakes to fix the position and orientation of the microscope 21. In other words, the support unit 23 includes brakes (e.g., a brake 45 illustrated in FIG. 3) for stopping the rotation of the moving parts of the first to sixth joints 232A to 232F relative to the respective fixed parts under the control of the controller 24.

The free movement mode is a mode of operation in which the brakes are released and the moving parts of the first to sixth joints 232A to 232F are allowed to rotate relative to the respective fixed parts, and in which direct operation by the operator is allowed such that, for example, the operator manually holds and directly moves the microscope 21 to adjust the position and orientation of the microscope 21.

The XY movement mode is a mode of operation in which the imaging field of view of the microscope 21 is moved in the X-axis direction or the Y-axis direction in accordance with the user operation performed by the operator on the foot switch 25. In other words, the support unit 23 includes actuators 4 that cause the second and the third joints 232B and 232C to move (cause the moving parts to rotate relative to the fixed parts) under the control of the controller 24. Detailed configuration of the actuators 4 will be described later.

The controller 24 performs first and second controls in the XY movement mode. Details of the first and the second controls will be described later.

The controller 24 performs various types of image processing (e.g., magnification processing by the electronic zooming capability) on an image signal output from the microscope 21, and outputs the image signal after image processing to the display device 3.

The foot switch 25 is operated by the operator by the foot, and is used in the XY movement mode as described above. Specifically, the foot switch 25 receives, from the operator, a move instruction to move the imaging field of view in +X direction, −X direction, +Y direction, or −Y direction. The foot switch 25 outputs an instruction signal corresponding to the move instruction to the controller 24.

In other words, the foot switch 25 includes a function of an operation receiver according to the present disclosure.

The operation receiver according to the present disclosure is not limited to the foot switch 25, and may be a hand-operated switch used by the operator by hand, for example.

The display device 3 is configured by a display such as a liquid crystal display or an organic electroluminescence (EL) display. The display device 3 displays an image on the basis of an image signal output from the microscope 21 and subjected to various types of image processing by the controller 24.

Use Example of Medical Observation System

Described next is a use example of the medical observation system 1 described above.

Figure 2:
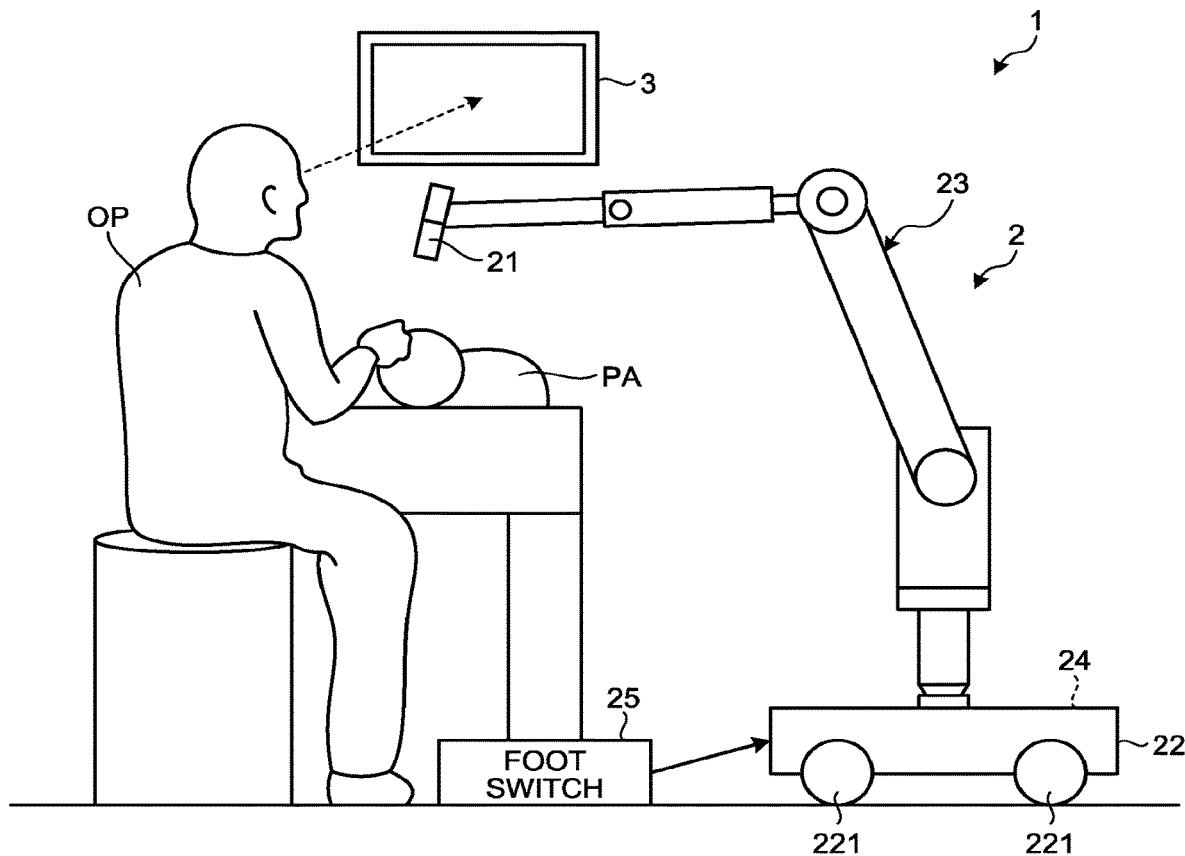
FIG. 2 is a diagram schematically illustrating a situation of a surgical operation using the medical observation system illustrated in FIG. 1.

FIG. 2 is a diagram schematically illustrating a situation of a surgical operation using the medical observation system 1.

First, an operator OP moves the microscope 21 in a position above an observation target of a patient PA (in the example of FIG. 2, the head of the patient PA) lying on an operating table. In the free movement mode, for example, the operator holds the microscope 21 to move it in a position above the observation target by using the six degrees of freedom of the support unit 23. In the XY movement mode, the operator operates the foot switch 25 (provides a move instruction to move the imaging field of view in the +X direction, −X direction, +Y direction, or −Y direction) to move the microscope 21 in a position above the observation target.

An image captured by the microscope 21 is magnified at a certain magnifying power by an optical zooming function of the microscope 21 and the electronic zooming function of the controller 24, and is displayed on the display device 3 attached on a wall of an operation room.

The operator OP performs the operation while checking the image displayed on the display device 3.

Configuration of Actuator

Described next is a configuration of the actuators 4 that actuate the second and the third joints 232B and 232C.

Figure 3:
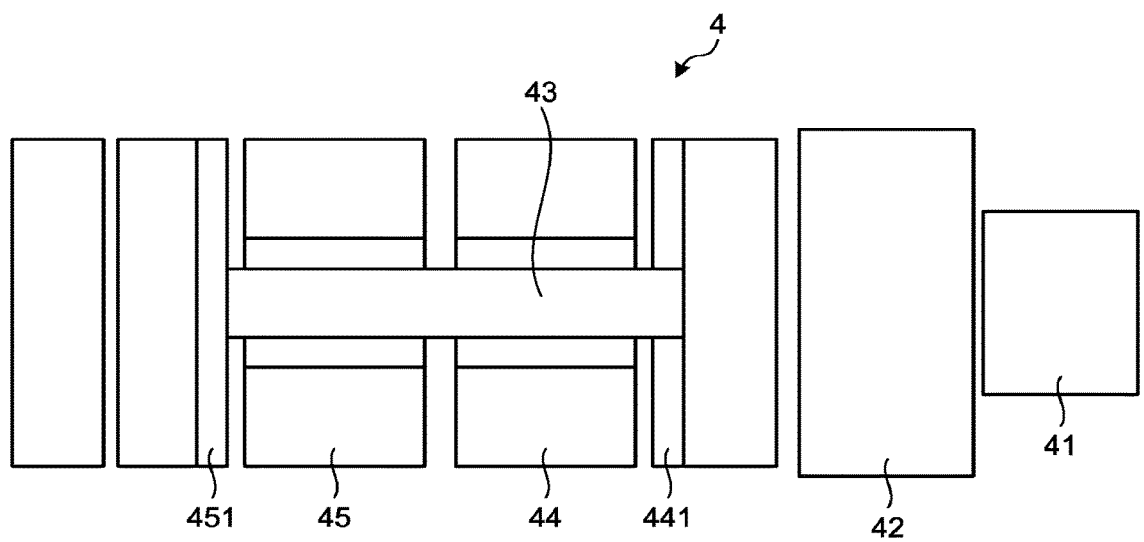
FIG. 3 is a diagram schematically illustrating a configuration of an actuator that actuates second and third joints illustrated in FIG. 1.

FIG. 3 is a diagram schematically illustrating a configuration of an actuator 4 that actuates the second and the third joints 232B and 232C.

The actuators 4 that actuate the second and the third joints 232B and 232C have the same configuration, and thus, like reference signs are assigned to like parts of the respective actuators 4.

As illustrated in FIG. 3, the actuator 4 includes a motor 41, a reduction mechanism 42, a drive shaft 43, a clutch 44, and a brake 45.

Figure 4:
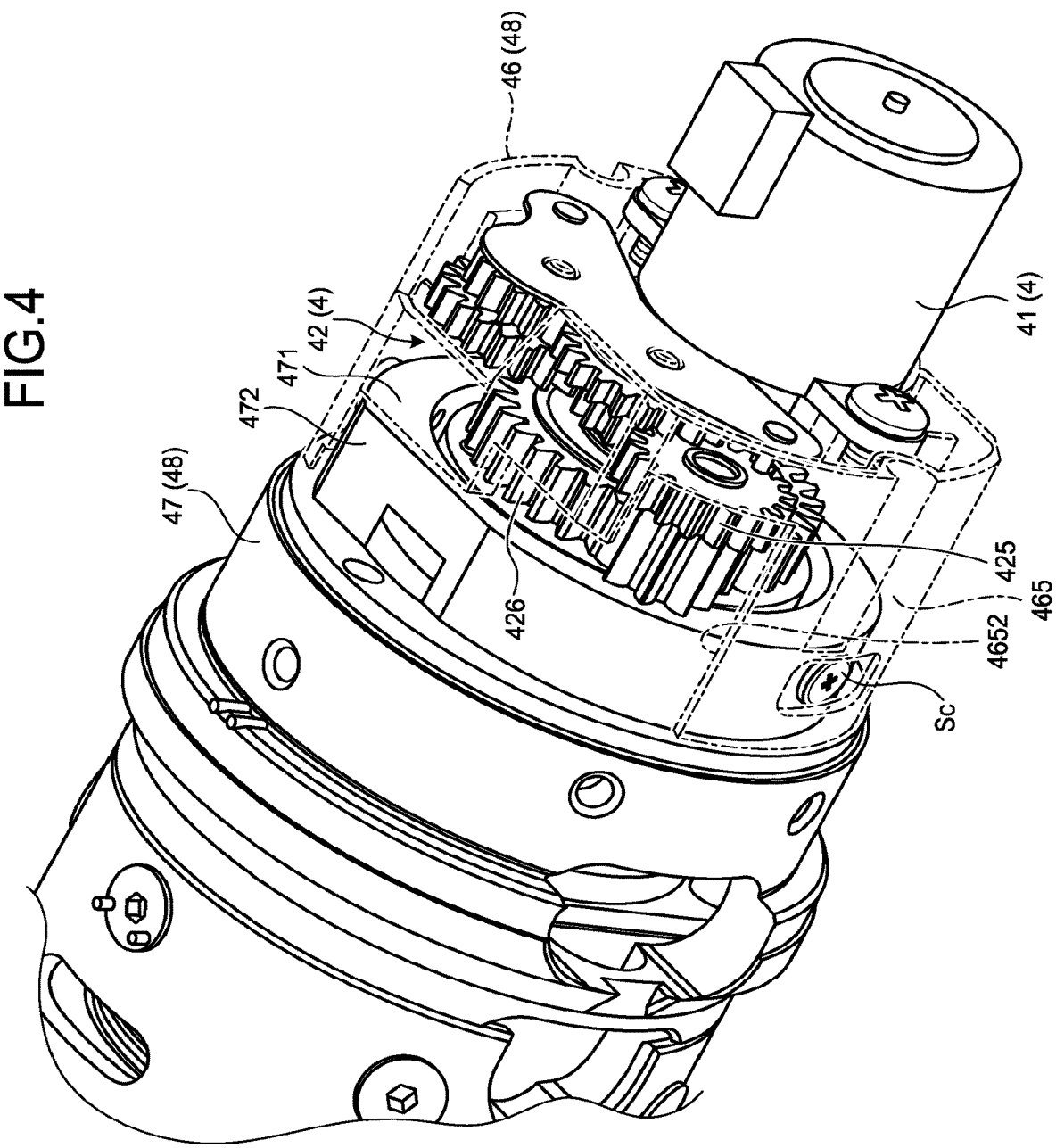
FIG. 4 is a diagram illustrating a motor and a reduction mechanism illustrated in FIG. 3.
Figure 5:
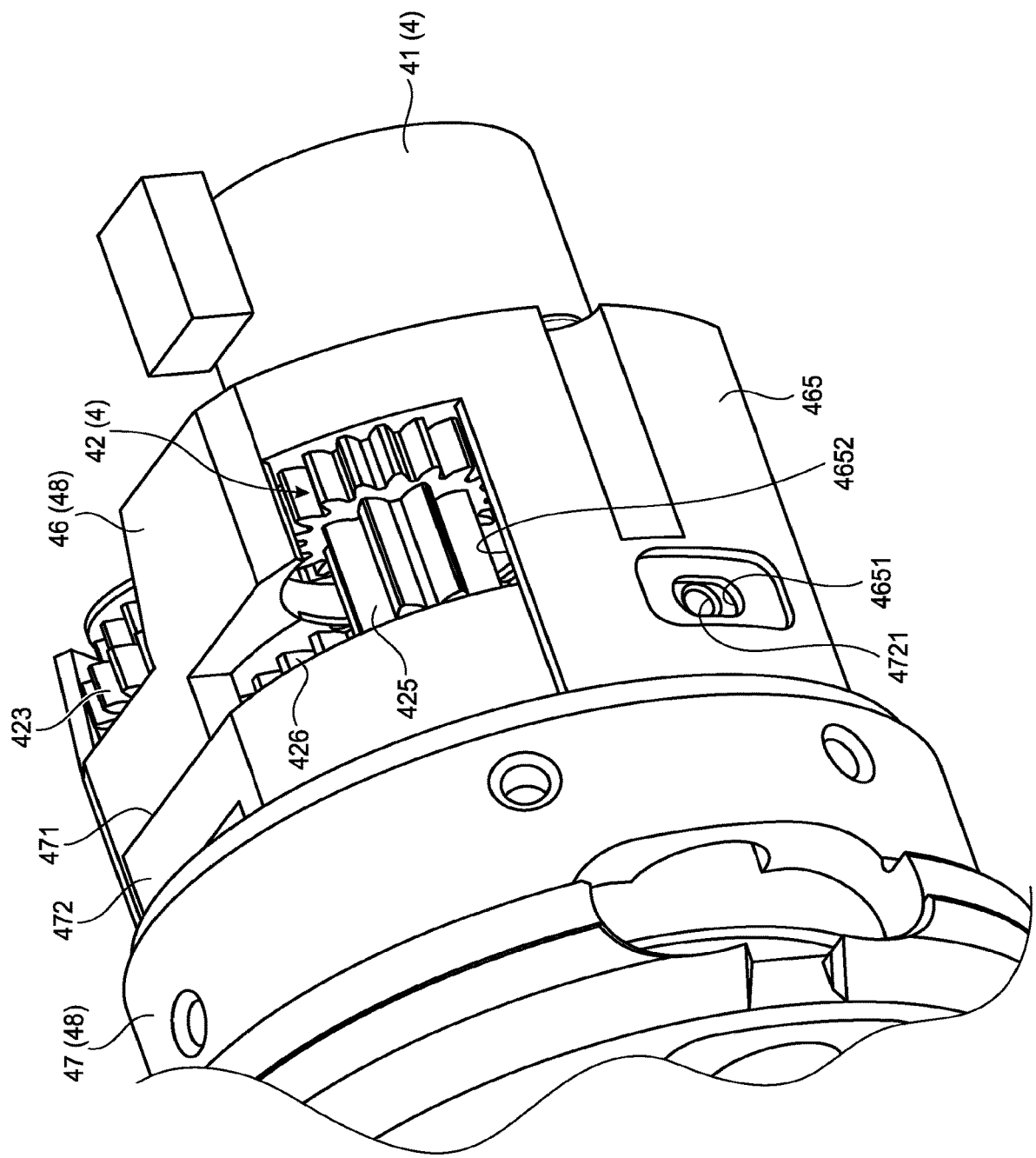
FIG. 5 is a diagram illustrating the motor and the reduction mechanism illustrated in FIG. 3.
Figure 6:
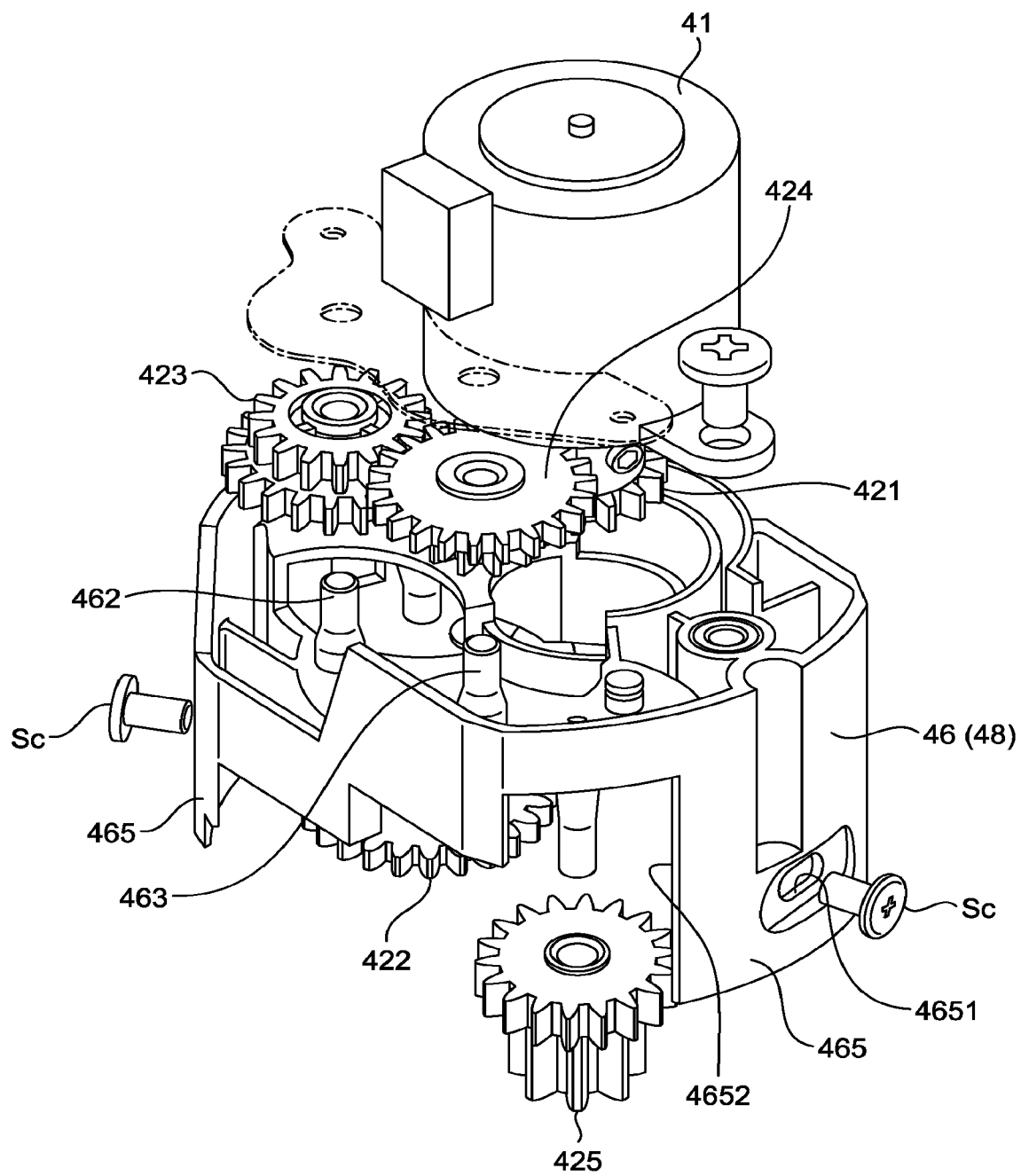
FIG. 6 is a diagram illustrating the motor and the reduction mechanism illustrated in FIG. 3.
Figure 7:
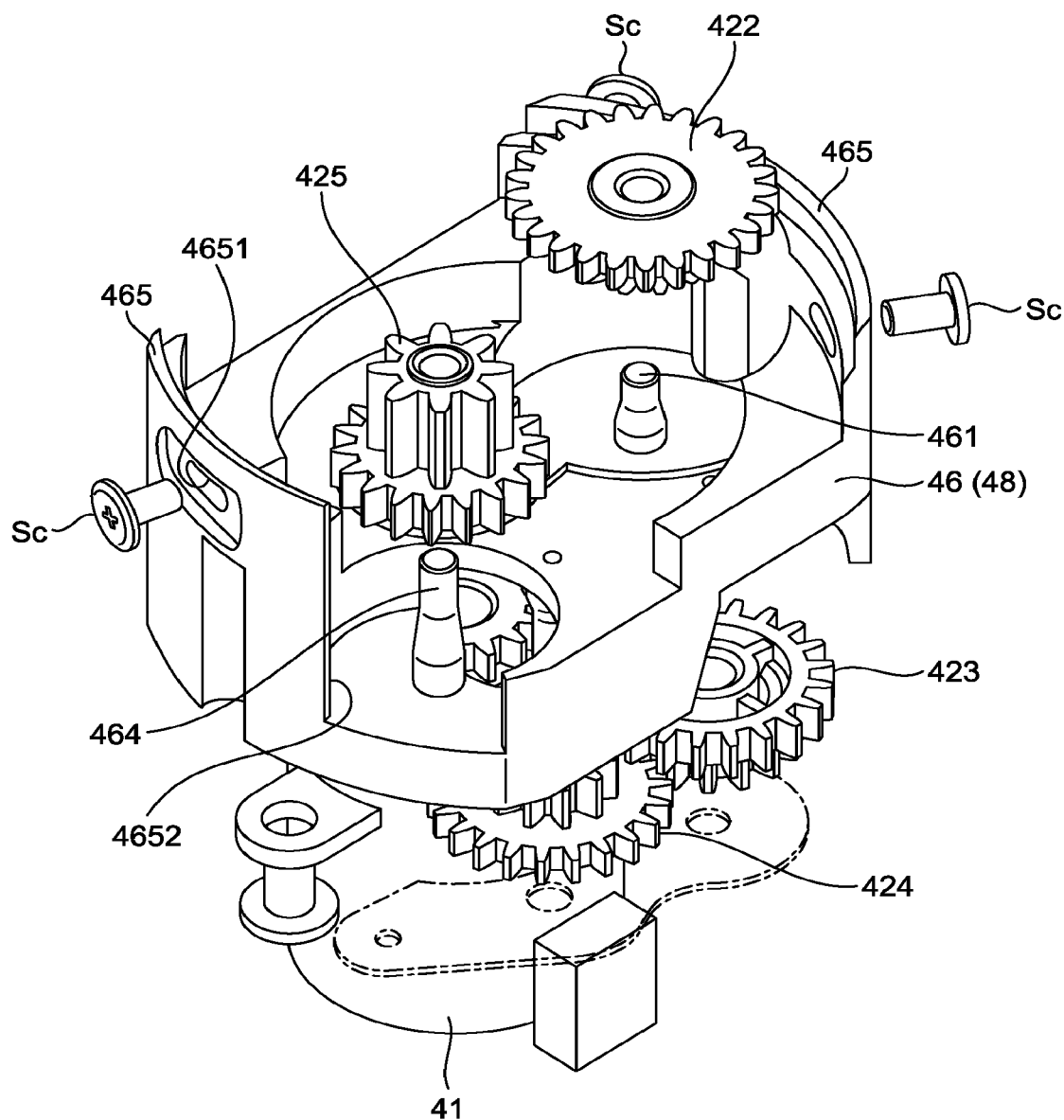
FIG. 7 is a diagram illustrating the motor and the reduction mechanism illustrated in FIG. 3.

FIGS. 4 to 7 are diagrams each illustrating the motor 41 and the reduction mechanism 42. Specifically, FIGS. 4 and 5 are perspective views illustrating a state in which the actuator 4 is installed in the support unit 23. FIGS. 6 and 7 are exploded perspective views of the motor 41 and the reduction mechanism 42.

The motor 41 is configured by, for example, a stepping motor controlled by the controller 24. The motor 41 is a power source that applies power to the second joint 232B (moving part) or the third joint 232C (moving part).

The reduction mechanism 42 is provided on the output shaft of the motor 41, and reduces the rotational speed of the output shaft at a certain reduction ratio. As illustrated in FIGS. 4 to 7, the reduction mechanism 42 includes first to sixth gears 421 to 426 disposed in this order from the output shaft of the motor 41. In the present embodiment, the first to sixth gears 421 to 426 are spur gears. In other words, the reduction mechanism 42 is disposed in a power transmission path from the motor 41 to the second joint 232B or to the third joint 232C and has a function of a gear mechanism according to the present disclosure.

In the present embodiment, five pairs of intermeshing gears in the first to sixth gears 421 to 426 are set such that the reduction ratio of the pairs increases in the order of disposition from the output shaft of the motor 41. In other words, the reduction ratio of the intermeshing first and second gears 421 and 422 is the lowest and that of the intermeshing fifth and sixth gears 425 and 426 is the highest.

The motor 41 and the first to fifth gears 421 to 425 of the reduction mechanism 42 are supported by a first support member 46 as illustrated in FIGS. 4 to 7. As illustrated in FIGS. 4 and 5, the sixth gear 426 is pivotally supported by a second support member 47 configured separately from the first support member 46, with the second support member 47 being exposed to the outside from an end portion 471.

The first support member 46 has a cylindrical shape with a bottom. The motor 41 is mounted on an external surface of the bottom of the first support member 46. The first gear 421 is attached to the output shaft of the motor 41. The second to fifth gears 422 to 425 are rotatably supported by first to fourth shafts 461 to 464 (FIGS. 6 and 7), respectively, provided on the external and internal surfaces of the bottom of the first support member 46.

The first and the second support members 46 and 47 are fitted (connected) together such that the end portion 471 of the second support member 47 is inserted into the first support member 46. Specifically, an inner surface of a side wall 465 (FIGS. 4 to 7) of the first support member 46 abuts an outer surface 472 (FIGS. 4 and 5) of the end portion 471 of the second support member 47. This configuration allows the fifth gear 425 that is pivotally supported by the first support member 46 and the sixth gear 426 that is pivotally supported by the second support member 47 to mesh together.

The first and the second support members 46 and 47 function as a backlash reduction mechanism 48 (FIGS. 4 to 7) that reduces an amount of backlash between the fifth and the sixth gears 425 and 426.

Figure 8:
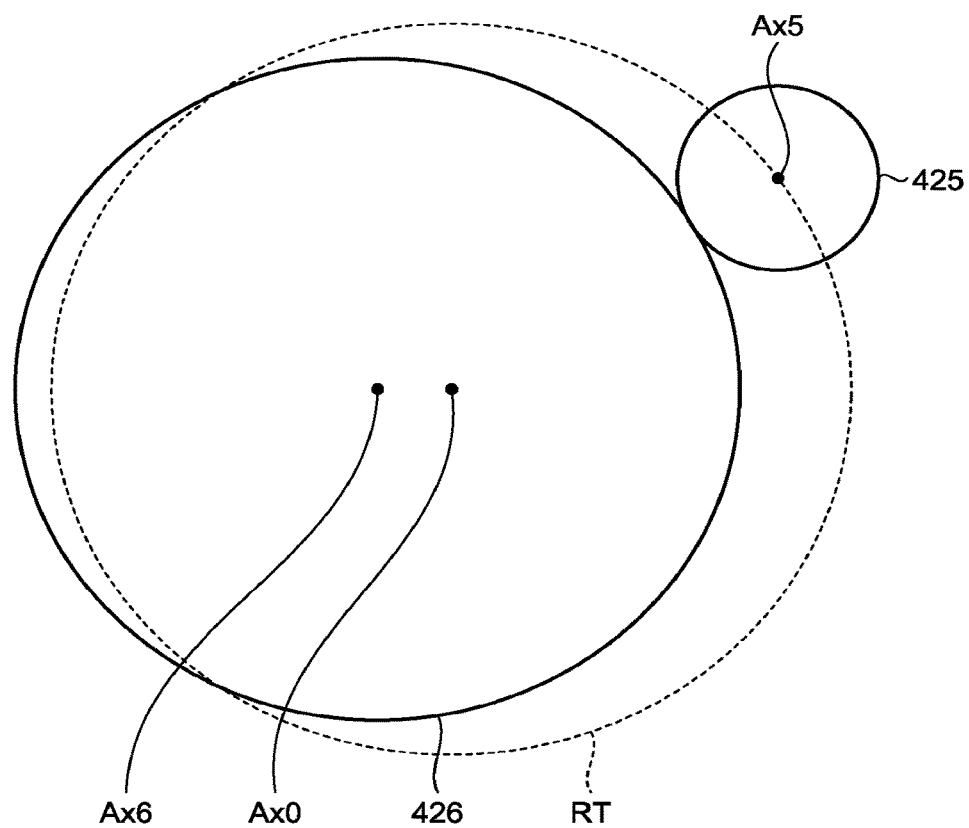
FIG. 8 is a diagram illustrating a method for adjusting an amount of backlash by using a backlash reduction mechanism illustrated in FIGS. 4 to 7.
Figure 9:
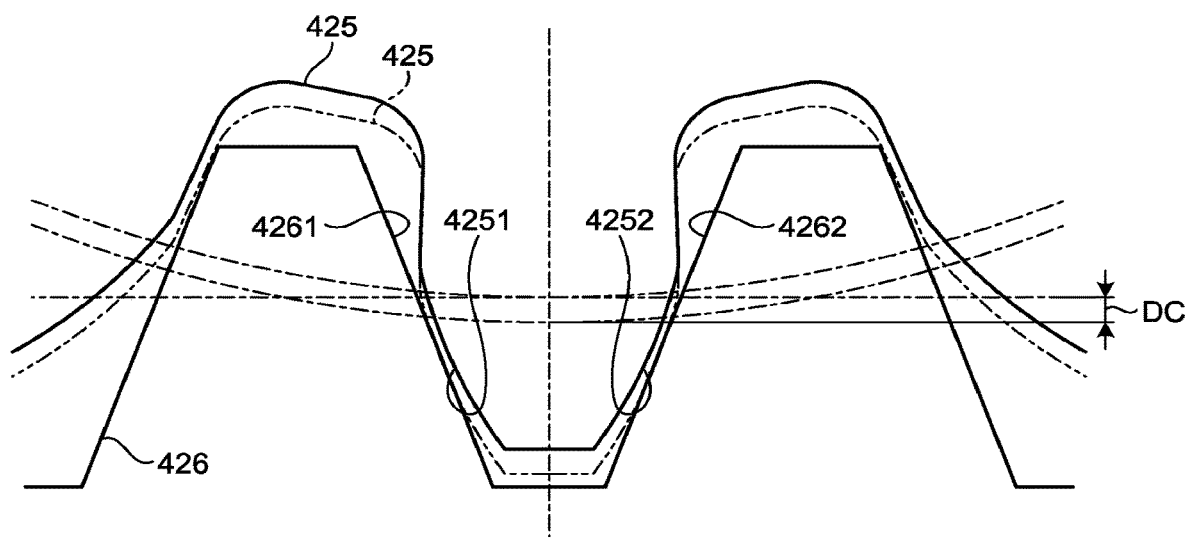
FIG. 9 is a diagram illustrating the method for adjusting the amount of backlash by using the backlash reduction mechanism illustrated in FIGS. 4 to 7.

FIGS. 8 and 9 are diagrams illustrating a method for adjusting the amount of backlash by using the backlash reduction mechanism 48. In FIG. 8, the fifth and sixth gears 425 and 426 are schematically illustrated in the form of circles. In FIG. 9, a state before the adjustment of an amount of backlash is drawn by a solid line, and a state after the adjustment is drawn by a two-dot-dash line.

The backlash reduction mechanism 48 is configured on the basis of the fact that an amount of backlash between intermeshing gears is adjusted by changing the center distance between the intermeshing gears.

Specifically, the abutting surfaces (the inner surface of the side wall 465 of the first support member 46 and the outer surface 472 of the second support member 47) are formed along a rotation trajectory about an axis Ax0 (FIG. 8) that is independent from a rotation axis Ax5 (FIG. 8) of the fifth gear 425 and a rotation axis Ax6 (FIG. 8) of the sixth gear 426, and is parallel to the rotation axes Ax5 and Ax6. The first support member 46 is rotatable about the axis Ax0 (hereinafter referred to as the rotation axis Ax0) relative to the second support member 47 with the inner surface of the side wall 465 sliding on the outer surface 472 of the second support member 47.

When the first support member 46 is rotated about the rotation axis Ax0, which is eccentric from the rotation axis Ax6 as described above, the center of the fifth gear 425 moves along a rotation trajectory RT as illustrated in FIG. 8. In other words, as illustrated in FIG. 8 or 9, this configuration changes the center distance between the fifth and the sixth gears 425 and 426 (in FIG. 9, an amount of change in the center distance is represented by DC). With this configuration, the amount of backlash between the fifth and the sixth gears 425 and 426 is adjusted.

The side wall 465 of the first support member 46 has a plurality of (three in the present embodiment) elongated through holes 4651 (FIGS. 5 to 7) elongated along the rotation trajectory RT about the rotation axis Ax0. The outer surface 472 of the second support member 47 has fixing holes 4721 (FIG. 5) provided in positions corresponding to the elongated through holes 4651.

The amount of backlash between the fifth and the sixth gears 425 and 426 are adjusted in the following manner.

First, an operator attaches a tape having a thickness equal to a desired amount of backlash to the tooth surface of the fifth gear 425.

Then, the operator fits the first and the second support members 46 and 47 together. The operator loosely fastens three fixing screws Sc (FIGS. 4, 6, and 7) to the three respective fixing holes 4721 through the three elongated through holes 4651 with the first support member 46 being kept rotatable about the rotation axis Ax0.

Subsequently, the operator rotates the first support member 46 about the rotation axis Ax0 relative to the second support member 47 until the tooth surfaces of the fifth and the sixth gears 425 and 426 abut each other via the attached tape.

The operator then tightly fastens the three fixing screws Sc to the fixing holes 4721 to fix the first support member 46 to the second support member 47.

Lastly, the operator removes the tape attached on the tooth surface of the fifth gear 425 through a cut-off portion 4652 (FIGS. 4 to 7) formed on the side wall 465.

An end of the drive shaft 43 is connected to the reduction mechanism 42 via the clutch 44 and the other end is connected to the second joint 232B (moving part) or the third joint 232C (moving part). The rotation of the motor 41 is transmitted to the drive shaft 43 via the clutch 44, and then the drive shaft 43 transmits the rotation of the motor 41 to the second joint 232B (moving part) or the third joint 232C (moving part), thereby causing the moving part to rotate about the second axis $O_2$ or the third axis $O_3$.

The clutch 44 is configured by an electromagnetic clutch (e.g., electromagnetic actuated clutch) controlled by the controller 24. The clutch 44 switches operating states between a permissive state and a disconnected state. The permissive state is a state in which an armature 441 (FIG. 3) is moved in the axial direction of the drive shaft 43 and connects the reduction mechanism 42 with the drive shaft 43 to allow transmission of power from the motor 41 to the drive shaft 43. The disconnected state is a state in which the drive shaft 43 is disconnected from the reduction mechanism 42 to shut off the power transmission.

In other words, the clutch 44 includes a function of a state switcher according to the present disclosure.

The brake 45 is configured by an electromagnetic brake (e.g., spring-actuated brake) that electrically switches release and restrain of the drive shaft 43 by moving an armature 451 (FIG. 3) in the axial direction of the drive shaft 43 under the control of the controller 24.

First and Second Controls by Controller

The controller 24 performs first and second controls described below in the XY movement mode.

The first control is a control on the motor 41 to move in accordance with an operation by the operator on the foot switch 25 (in accordance with a move instruction to move the imaging field of view in the +X direction, −X direction, +Y direction, or −Y direction).

Specifically, when the operation on the foot switch 25 is a move instruction to move the imaging field of view in the +X direction, the controller 24 causes the motor 41 that is the power source for the second joint 232B (moving part) to rotate in a first direction (hereinafter referred to as rotate in a forward direction). When the operation on the foot switch 25 is a move instruction to move the imaging field of view in the −X axis direction, the controller 24 causes the motor 41 that is the power source for the second joint 232B to rotate in a second direction (hereinafter referred to as rotate in a reverse direction) that is opposite to the first direction. When the operation on the foot switch 25 is a move instruction to move the imaging field of view in the +Y direction, the controller 24 causes the motor 41 that is the power source for the third joint 232C (moving part) to rotate in the forward direction. When the operation on the foot switch 25 is a move instruction to move the imaging field of view in the −Y direction, the controller 24 causes the motor 41 that is the power source for the third joint 232C (moving part) to rotate in the reverse direction.

The second control is performed after the first control is completed and the rotation of the motor 41 is stopped. The second control is a control on the motor 41 to rotate the motor 41 in a reverse direction relative to the direction in which the motor 41 is rotated in the first control. The second control is performed to adjust the distance between the tooth surfaces of the fifth and the sixth gears 425 and 426 that mesh with each other in accordance with the rotation of the motor 41 in the reverse direction and the distance between the tooth surfaces thereof that are out of meshing engagement with each other in accordance with the rotation of the motor 41 in the reverse direction to a value corresponding to half the amount of backlash (the amount of backlash after adjustment by the backlash reduction mechanism 48) between the fifth and the sixth gears 425 and 426.

The tooth surfaces that mesh with each other in accordance with the rotation of the motor 41 in the reverse direction correspond to one of a pair of tooth surfaces 4251 and 4261 and a pair of tooth surfaces 4252 and 4262 illustrated in FIG. 9. One of the pairs of the tooth surfaces corresponds to first tooth surfaces according to the present disclosure, and the distance between the pair of the tooth surfaces corresponds to a first distance according to the present disclosure. The tooth surfaces that are out of meshing engagement with each other in accordance with the rotation of the motor 41 in the reverse direction correspond to the other one of the pair of the tooth surfaces 4251 and 4261 and the pair of the tooth surfaces 4252 and 4262. The other one of the pairs of the tooth surfaces corresponds to second tooth surfaces according to the present disclosure, and the distance between the pair of the tooth surfaces corresponds to a second distance according to the present disclosure. In other words, the second control is performed to adjust the distance between the tooth surfaces 4251 and 4261 and the distance between the tooth surfaces 4252 and 4262 to a value corresponding to half the amount of backlash between the fifth and the sixth gears 425 and 426 (adjust the first and the second distances to a value corresponding to half the amount of backlash).

The following describes in detail the procedure of the first and the second controls.

Figure 10:
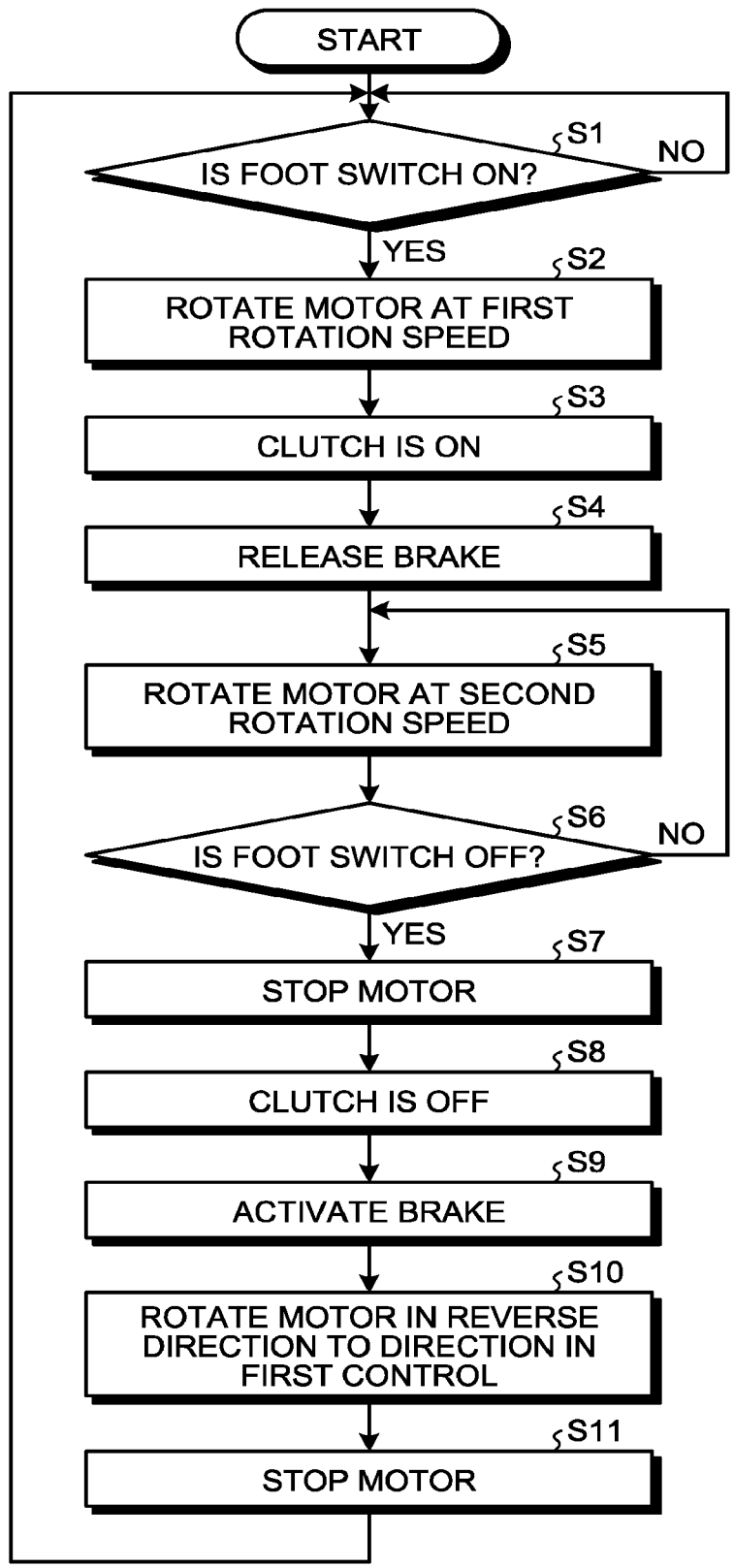
FIG. 10 is a flowchart illustrating first and second controls performed by a controller illustrated in FIG. 1.

FIG. 10 is a flowchart illustrating the first and the second controls performed by the controller 24.

The first control corresponds to Steps S1 to S7 illustrated in FIG. 10. The second control corresponds to Steps S8 to S11 illustrated in FIG. 10.

For the sake of convenience, the tooth surfaces that mesh with each other in accordance with the rotation of the motor 41 in the second control are determined to be the tooth surfaces 4251 and 4261 (hereinafter referred to as first tooth surfaces 4251 and 4261) and the distance between the first tooth surfaces 4251 and 4261 is determined to be a first distance, in the following description. The tooth surfaces that are out of meshing engagement with each other in accordance with the rotation of the motor 41 in the second control are determined to be the tooth surfaces 4252 and 4262 (hereinafter referred to as second tooth surfaces 4252 and 4262) and the distance between the second tooth surfaces 4252 and 4262 is determined to be a second distance, in the following description. As described above, the motor 41 is rotated in the opposite directions in the first control performed immediately before the second control and in the second control. Thus, the tooth surfaces that mesh with each other in accordance with the rotation of the motor 41 in the first control are the second tooth surfaces 4252 and 4262, and the tooth surfaces that are out of meshing engagement with each other are the first tooth surfaces 4251 and 4261.

The following description starts on the assumption that the second control (Steps S8 to S11) has been performed and the first and the second distances have the same value (a value corresponding to half the amount of backlash between the fifth and the sixth gears 425 and 426). For the sake of convenience, the amount of backlash is determined to be 1.0 mm in the following description. The following description starts from a state in which the second control (Steps S8 to S11) has been performed and the operating state has been switched to the disconnected state (clutch is off), and a state in which the brake 45 is activated (the drive shaft 43 is restrained).

First, the controller 24 constantly monitors whether the operator operates the foot switch 25 (whether the foot switch 25 is switched on), that is, whether the operator provides a move instruction to move the imaging field of view in the +X direction, −X direction, +Y direction, or −Y direction (Step S1).

If the controller 24 determines that the foot switch 25 is switched on (Yes at Step S1), the controller 24 causes the motor 41 corresponding to the move instruction at Step S1 to rotate at a first rotation speed in a direction in accordance with the move instruction (Step S2). At Step S2, for example, the controller 24 outputs pulse signals at 2000 pulses per second to the motor 41 for a duration of 0.25 second to rotate the motor 41 at the first rotation speed.

With this process, the second tooth surfaces 4252 and 4262 abut each other, and the first and the second distances, each of which was 0.5 mm corresponding to half the amount of backlash between the fifth and the sixth gears 425 and 426, are changed such that the second distance is zero and the first distance is 1.0 mm that is the same as the amount of backlash.

The controller 24 then controls the clutch 44 to switch from the disconnected state (clutch is off) to the permissive state (clutch is on) (Step S3), and controls the brake 45 to release the brake 45 (release the drive shaft 43) (Step S4).

The controller 24 causes the motor 41 corresponding to the move instruction at Step S1 to rotate at a second rotation speed that is lower than the first rotation speed in a direction in accordance with the move instruction (the same direction as that in Step S2) (Step S5). At Step S5, for example, the controller 24 outputs pulse signals at 200 pulses per second to the motor 41 to rotate the motor 41 at the second rotation speed, which corresponds to one tenth of the first rotation speed.

The controller 24 constantly monitors whether the operation on the foot switch 25 performed by the operator at Step S1 is released (whether the foot switch 25 is switched off) (Step S6). As long as this operation continues, the controller 24 continues performing the process at Step S5. If the controller 24 determines that the foot switch 25 is switched off (Yes at Step S6), the controller 24 ends the process at Step S5 (causes the motor 41 to stop rotating at the second rotation speed) (Step S7).

In other words, in the processes from Step S3 to Step S7, the rotation of the motor 41 is transmitted to the second joint 232B (moving part) or the third joint 232C (moving part) while the foot switch 25 is activated by the operator, and the imaging field of view of the microscope 21 is moved in the +X direction, −X direction, +Y direction, or −Y direction.

After the first control (Steps S1 to S7), the controller 24 performs the second control (Steps S8 to S11).

First, the controller 24 controls the clutch 44 to switch from the permissive state (clutch is on) to the disconnected state (clutch is off) (Step S8), and controls the brake 45 to activate the brake 45 (restrain the drive shaft 43) (Step S9).

The controller 24 then causes the motor 41 to rotate in the reverse direction relative to the direction in which the motor 41 rotates in the first control (Step S1 to S7) at the first rotation speed (Step S10). At Step S10, for example, the controller 24 outputs pulse signals at 2000 pulses per second to the motor 41 for a duration of 0.25 second to rotate the motor 41 at the first rotation speed in the reverse direction, and then causes the motor 41 to stop rotating (Step S11). The controller 24 returns the process to Step S1.

After the first control, the second distance is zero and the first distance is 1.0 mm that is the same as the amount of backlash between the fifth and the sixth gears 425 and 426, and after the second control, the first and the second distances are adjusted to 0.5 mm corresponding to half the amount of backlash.

The medical observation device 2 according to the embodiment above performs the first control for causing the motor 41 to rotate in accordance with a user operation on the foot switch 25, and, after the first control is completed and rotation of the motor 41 is stopped, performs the second control for adjusting the first and the second distances to a value corresponding to half the amount of backlash between the fifth and the sixth gears 425 and 426. In other words, in the first control, the first distance has the same value as the amount of backlash between the fifth and the sixth gears 425 and 426, and the second distance is zero. The second control is performed after the first control, and the first and the second distances are adjusted to a value corresponding to half the amount of backlash between the fifth and the sixth gears 425 and 426.

When a user operation is performed on the foot switch 25 after the first and the second controls to perform a next first control in which the motor 41 is rotated in the reverse direction relative to the direction in the previous first control (the same direction as that in the second control), moving the motor 41 for the first distance having a value corresponding to half the amount of backlash between the fifth and the sixth gears 425 and 426 is sufficient to engage the fifth gear 425 with the sixth gear 426. Thus, the rotation of the motor 41 may be transmitted to the second joint 232B (moving part) or the third joint 232C (moving part), that is, the position and orientation of the microscope 21 may be changed (the imaging field of view of the microscope 21 may be moved).

The medical observation device 2 according to the present embodiment may reduce the idle running time between the fifth and the sixth gears 425 and 426 even when the medical observation device 2 performs a first control for causing the motor 41 to rotate in the reverse direction that is opposite to the direction in the immediately previous first control, and thus, the imaging field of view of the microscope 21 may be moved immediately.

In particular, performing the second control adjusts the first and the second distances to a value corresponding to half the amount of backlash between the fifth and the sixth gears 425 and 426. When a user operation is performed on the foot switch 25 after the first and the second controls to perform a next first control in which the motor 41 is rotated in the same direction as that in the previous first control (the reverse direction that is opposite to the direction in the second control), moving the motor 41 for the second distance having a value corresponding to half the amount of backlash between the fifth and the sixth gears 425 and 426 is sufficient to engage the fifth gear 425 with the sixth gear 426. Thus, the rotation of the motor 41 may be transmitted to the second joint 232B (moving part) or the third joint 232C (moving part).

This configuration allows the fifth and the sixth gears 425 and 426 to experience an idle running time for an equal time in both cases in which the first control is performed to rotate the motor 41 in the reverse direction that is opposite to the direction in the immediately previous first control, and in which the first control is performed to rotate the motor 41 in the same direction as that in the immediately previous first control. This configuration may prevent giving the operator a sense of incongruity in performing the first control in both cases.

When the medical observation device 2 according to the present embodiment performs the first control after the second control, the medical observation device 2 rotates the motor 41 at first rotation speed until the first or second distance is reduced to zero (at Step S2 above, until the second distance is reduced to zero). After the distance is reduced to zero, the medical observation device 2 rotates the motor 41 at second rotation speed slower than the first rotation speed.

The medical observation device 2 rotates the motor 41 at the first rotation speed, which is relatively fast speed, when the medical observation device 2 performs the first control after the second control. This configuration may further reduce the idle running time between the fifth and the sixth gears 425 and 426 and may move the imaging field of view more immediately.

In the first control, rotating the motor 41 at the relatively fast first rotation speed in the permissive state (clutch is on) may cause loss of synchronization of the motor 41 due to an excessive load.

The medical observation device 2 according to the present embodiment rotates the motor 41 at the relatively fast first speed in the disconnected state (clutch is off, a state in which an excessive load is not placed on the motor 41) in the first control. This configuration may prevent loss of synchronization of the motor 41.

The medical observation device 2 according to the present embodiment includes the backlash reduction mechanism 48 that is configured by the first support member 46 that pivotally supports the fifth gear 425 and the second support member 47 that pivotally supports the sixth gear 426. The backlash reduction mechanism 48 is configured to reduce an amount of backlash between the fifth and the sixth gears 425 and 426.

The amount of backlash between the fifth and the sixth gears 425 and 426 may be reduced by such a simple configuration. Moreover, reducing the amount of backlash may further reduce the idle running time between the fifth and the sixth gears 425 and 426. This configuration may more immediately move the imaging field of view.

In particular, using the backlash reduction mechanism 48 that mechanically reduces the amount of backlash and using the configuration for adjusting the first and the second distances to a value corresponding to half the amount of backlash may efficiently reduce the idle running time between the fifth and the sixth gears 425 and 426.

The backlash reduction mechanism 48 reduces the amount of backlash between the fifth and the sixth gears 425 and 426 having the largest reduction ratio of the ratios of the five pairs of intermeshing gears among the first to the sixth gears 421 to 426. In other words, reducing the amount of backlash between the fifth and the sixth gears 425 and 426 is more effective in terms of reduction ratio than reducing the amount of backlash in any other pairs of gears having smaller reduction ratios.

Other Embodiments

The embodiment of the present disclosure is described above, but the embodiment is not intended to limit the scope of the present disclosure.

In the second control according to the embodiment above (Steps S8 to S11), the first and the second distances are adjusted to a value corresponding to half the amount of backlash. However, the second control may adjust the first and the second distances to any value other than the value corresponding to half the amount of backlash as long as the first and the second distances have a smaller value than the amount of backlash.

In the first control according to the embodiment above (Steps S1 to S7), Step S2 (the motor 41 is rotated at the first rotation speed) is performed with the clutch being off, but is not limited to this. Step S2 may be performed with the clutch being on. Step S2 is performed with the brake 45 being activated, but is not limited to this. Step S2 may be performed with the brake 45 being released. In other words, Steps S3 and S4 may be performed before Step S2.

In the second control according to the embodiment above (Steps S8 to S11), the motor 41 is rotated at the first rotation speed at Step S10, but is not limited to this. The motor 41 may be rotated at the second rotation speed at Step S10.

In the embodiment above, the reduction mechanism 42 is used as the gear mechanism according to the present disclosure, but is not limited to this. For example, a power transmission mechanism (not illustrated) that includes a plurality of gears and connects the other end of the drive shaft 43 with the second or the third joint 232B or 232C (moving part) may be used as the gear mechanism according to the present disclosure.

In the embodiment above, the backlash reduction mechanism 48 is configured such that the first support member 46 is rotatable about the rotation axis Ax0 relative to the second support member 47, but is not limited to this. The backlash reduction mechanism 48 may be configured by any mechanism that may change the center distance between the intermeshing fifth and sixth gears 425 and 426.

Figure 11:
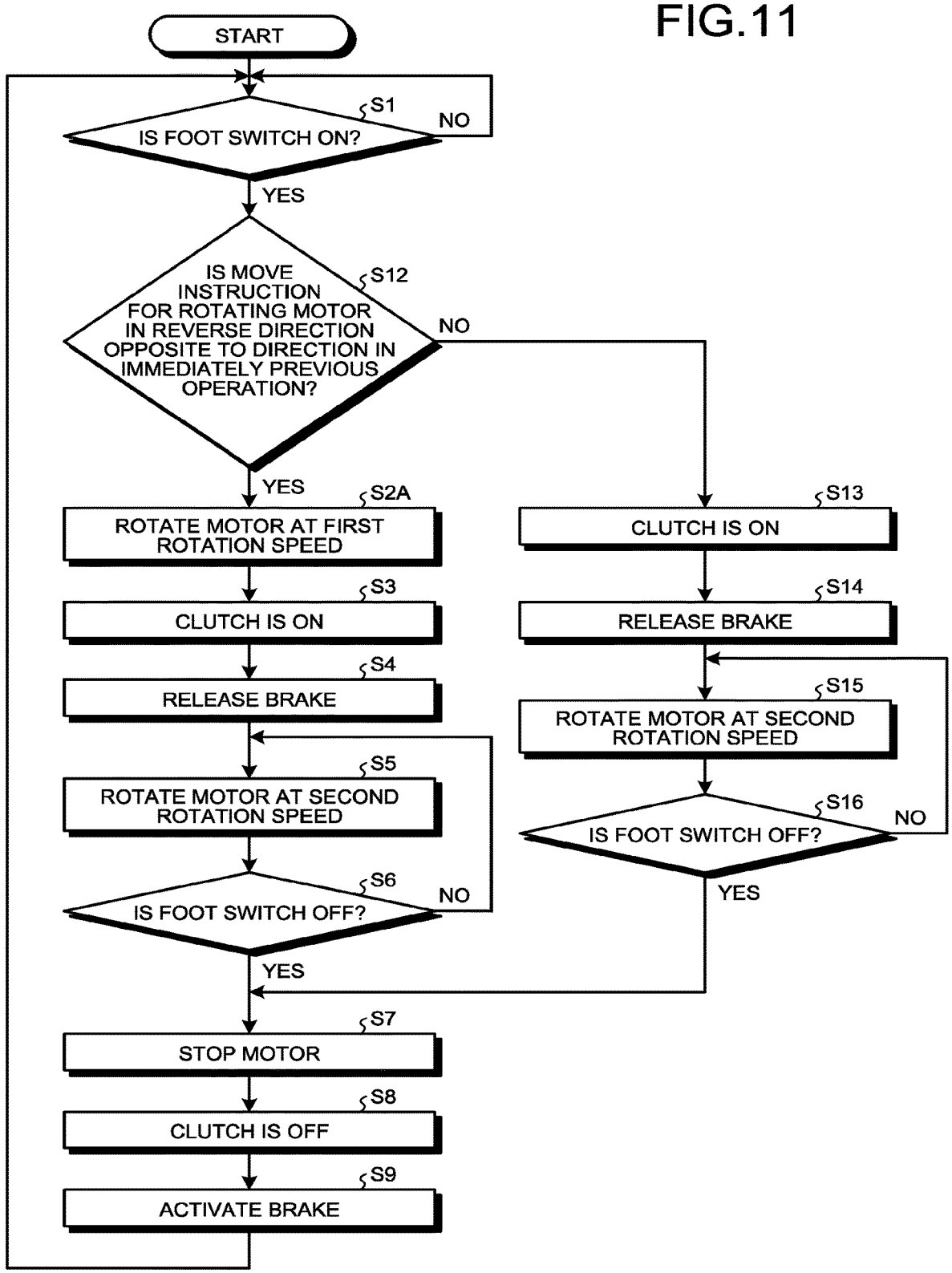
FIG. 11 is a diagram illustrating a modification of the embodiment of the present disclosure.

FIG. 11 is a diagram illustrating a modification of the embodiment of the present disclosure.

The controller 24 may perform the procedure illustrated in FIG. 11 as the operation in the XY movement mode in the embodiment above.

The following description starts with one of the distance between the tooth surfaces 4251 and 4261 and the distance between the tooth surfaces 4252 and 4262 being zero and the other one of the distances having the same value as the amount of backlash between the fifth and the sixth gears 425 and 426. For the sake of convenience, the amount of backlash is determined to be 1.0 mm in the same manner as in the embodiment above. The following description starts with the operating state being switched to the disconnected state (clutch being off) and the brake 45 being activated (the drive shaft 43 being restrained) in the same manner as in the embodiment above.

As illustrated in FIG. 11, the procedure according to the present modification differs from the procedure according to the embodiment above (FIG. 10) in that Steps S10 and S11 are excluded, Step S2A is included instead of Step S2, and Steps S12 to S16 are additionally included.

Thus, the following only describes Steps S2A, and S12 to S16.

Step S12 is performed if the controller 24 determines that the foot switch 25 is switched on (Yes at Step S1).

Specifically, at Step S12, the controller 24 determines whether the move instruction at Step S1 is an instruction for rotating the motor 41 in the reverse direction that is opposite to the direction in the immediately previous operation.

For example, when the motor 41 is rotated in the forward direction in the immediately previous operation and the move instruction at Step S1 is for rotating the motor 41 in the reverse direction, the controller 24 makes a "yes" determination at Step S12. When the motor 41 is rotated in the forward direction in the immediately previous operation and the move instruction at Step S1 is for rotating the motor 41 in the forward direction, the controller 24 makes a "no" determination at Step S12.

Step S2A is performed if the controller 24 makes a "yes" determination at Step S12.

Specifically, at Step S2A, the controller 24 rotates the motor 41 corresponding to the move instruction at Step S1 at the first rotation speed in a direction corresponding to the move instruction. For example, the controller 24 outputs pulse signals at 2000 pulses per second to the motor 41 for a duration of 0.5 second to rotate the motor 41 at the first rotation speed.

Before this process, one of the distance between the tooth surfaces 4251 and 4261 and the distance between the tooth surfaces 4252 and 4262 is zero and the other one of the distances is 1.0 mm that is the same value as the amount of backlash between the fifth and the sixth gears 425 and 426. After this process, the tooth surfaces 4251 and 4261 or 4252 and 4262 that have been separate from each other abut each other and thus the distance therebetween is zero, and the distance between the other pair of the tooth surfaces is 1.0 mm that is the same value as the amount of backlash.

After Step S2A, the controller 24 performs Steps S3 to S9 described in the embodiment above, and then, the process returns to Step S1.

Steps S13 to S16 are performed if the controller 24 makes a "no" determination at Step S12. Steps S13 to S16 are the same processes as those of Steps S3 to S6.

If the controller 24 determines that the foot switch 25 is switched off (Yes at Step S16), the controller 24 performs the process at Step S7.

In other words, in Steps S13 to S16, the motor 41 is rotated in the same direction as that in the immediately previous operation. Thus, one of the distance between the tooth surfaces 4251 and 4261 and the distance between the tooth surfaces 4252 and 4262 is still zero, and the distance between the other pair of the tooth surfaces is still 1.0 mm that is the same value as the amount of backlash between the fifth and the sixth gears 425 and 426.

In the embodiment above, the controller 24 moves the imaging field of view of the microscope 21 in the +X direction, −X direction, +Y direction, or −Y direction in accordance with the user operation on the foot switch 25 by the operator in the XY movement mode, but is not limited to this. For example, the controller 24 may move the imaging field of view of the microscope 21 in accordance with the move instruction from an external device instructing, for example, the direction and the amount of the movement of the imaging field of view.

With such a configuration, the aforementioned problem relating to the backlash occurs. For example, when the external device sends a move instruction for moving the imaging field of view in the −X direction and then sends a move instruction for moving the imaging field of view in the +X direction by 5 mm immediately after the previous operation, in which the motor 41 is going to rotate in the reverse direction that is opposite to the direction in the immediately previous operation, the fifth and the sixth gears 425 and 426 experience an idle running time due to backlash and the imaging field of view may not be moved as instructed (for example, the imaging field of view is moved only by 4 mm instead of 5 mm in the +X direction).

In this case, the controller 24 compares the immediately previous move instruction with the current move instruction and determines whether the current move instruction is for rotating the motor 41 in the reverse direction that is opposite to the direction in the immediately previous instruction. If the controller 24 makes a "yes" determination, the controller 24 corrects the move amount contained in the current move instruction to a move amount to which the amount of backlash is added (the controller 24 corrects, for example, a move amount of 5 mm to 6 mm that includes the amount of backlash), and moves the imaging field of view of the microscope 21 by the corrected move amount. This configuration allows the imaging field of view to be moved as instructed.

In the medical observation device according to the present disclosure, the controller performs the first control for causing the motor to rotate in accordance with a user operation on the operation receiver, and, after the first control is completed and the rotation of the motor is stopped, performs the second control to adjust the first and the second distances to a smaller value than the amount of backlash between two gears. In other words, in the first control, the first distance has the same value as the amount of backlash between the two gears, and the second distance is zero. The second control is performed after the first control, and the first and the second distances are adjusted to a smaller value than the amount of backlash between the two gears.

When a user operation is performed on the operation receiver after the first and the second controls to perform a next first control in which the motor is rotated in the reverse direction that is opposite to the direction in the previous first control, moving the motor for the first distance having a smaller value than the amount of backlash between the two gears is sufficient to engage the two gears with each other. Thus, the rotation of the motor may be transmitted to the joint, that is, the position and orientation of the image-capturing unit may be changed (the imaging field of view may be changed).

The medical observation device according to the present disclosure may reduce the idle running time between the two gears when the medical observation device performs a first control that causes the motor to rotate in the reverse direction that is opposite to the direction in the immediately previous first control, and thus, the imaging field of view of the microscope 21 may be moved immediately.

It should be understood by those skilled in the art that various modifications, combinations, sub-combinations and alterations may occur depending on design requirements and other factors insofar as they are within the scope of the appended claims or the equivalents thereof.

What is claimed is:

1. A medical observation device comprising:
an imaging device configured to capture an observation target;
a structural support that supports the imaging device at a distal end and includes a plurality of arms and a plurality of joints rotatably connecting the arms;
a motor that is provided in the structural support, applies power to at least one joint of the plurality of joints, and rotates two of the arms connected at the at least one joint relative to each other;
a gear mechanism that includes two intermeshing gears and is disposed in a power transmission path from the motor to the at least one joint;
an operation receiver that receives a user operation; and
a controller configured to perform a first control operation that causes the motor to rotate in accordance with the user operation received by the operation receiver and perform a second control operation after the first control operation is completed and rotation of the motor is stopped, wherein
the controller is further configured to perform the second control operation to rotate the motor in a reverse direction that is opposite to a direction in which the motor is rotated in the first control operation so that a first distance between first tooth surfaces of the two intermeshing gears, the first tooth surfaces meshing with each other in accordance with rotation of the motor in the reverse direction, and a second distance between second tooth surfaces of the two intermeshing gears, the second tooth surfaces being out of meshing engagement with each other in accordance with the rotation of the motor in the reverse direction, are respectively set to values smaller than an amount of backlash between the two intermeshing gears.

2. The medical observation device according to claim 1, wherein the controller is further configured to perform the second control operation to adjust each of the first distance and the second distance to half the amount of backlash.

3. The medical observation device according to claim 1, wherein, when the controller is further configured to
   perform the first control operation after the second control operation,
   rotate the motor at first rotation speed until the first distance or the second distance is reduced to zero, and
   rotate the motor at second rotation speed slower than the first rotation speed after the first distance or the second distance is reduced to zero.

4. The medical observation device according to claim 3, wherein
   the power transmission path includes a state switcher provided between the gear mechanism and the at least one joint, the state switcher being configured to switch between a disconnected state and a permissive state, the disconnected state being a state in which transmission of power from the gear mechanism to the at least one joint is shut off, and the permissive state being a state in which the transmission of power is permitted, and
   the controller is further configured to rotate the motor at the first rotation speed in the disconnected state, and rotate the motor at the second rotation speed in the permissive state.

5. The medical observation device according to claim 1, further comprising:
   a first support that supports one of the two intermeshing gears rotatably about an axis; and
   a second support that is separate from the first support and supports another of the two intermeshing gears rotatably about an axis, wherein
   the first support member and the second support member are coupled with each other so as to mesh the two intermeshing gears with each other, and
   the first support is movable relative to the second support and is configured to change the amount of backlash between the two intermeshing gears by being moved relative to the second support.

6. The medical observation device according to claim 5, wherein
   the two intermeshing gears are spur gears,
   the first support is rotatable relative to the second support and configured to change the amount of backlash between the two intermeshing gears by rotating relative to the second support, and
   the first support has a rotation axis that is independent from the axes of the two intermeshing gears and is parallel to the axes.

7. The medical observation device according to claim 5, wherein
   the gear mechanism includes three or more gears that include the two intermeshing gears and configured as a reduction mechanism that reduces rotational speed of the motor, and
   the two intermeshing gears have a largest reduction ratio of reduction ratios of a plurality of pairs of intermeshing gears in the reduction mechanism.

8. The medical observation device according to claim 1, wherein the imaging device is configured to capture a magnified image of the observation target.

* * * * *